United States Patent
Kulprathipanja et al.

(10) Patent No.: US 6,506,935 B1
(45) Date of Patent: Jan. 14, 2003

(54) COMBINATION PRETREATMENT/ADSORPTION FOR TREATING A LIQUID STREAM CONTAMINATED WITH AN IODINE-CONTAINING COMPOUND

(75) Inventors: Santi Kulprathipanja, Inverness, IL (US); Bipin V. Vora, Naperville, IL (US); William A. Leet, Yorktown, VA (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/905,454

(22) Filed: Jul. 13, 2001

Related U.S. Application Data

(63) Continuation-in-part of application No. 09/459,100, filed on Dec. 13, 1999, now abandoned, which is a continuation-in-part of application No. 09/211,791, filed on Dec. 15, 1998, now Pat. No. 6,380,428, which is a continuation-in-part of application No. 09/035,798, filed on Mar. 6, 1998, now Pat. No. 5,962,735.

(51) Int. Cl.[7] .......................... C07C 51/42; C07B 53/00
(52) U.S. Cl. ........................................ 562/608; 562/606
(58) Field of Search ................................ 562/608, 606

(56) References Cited

U.S. PATENT DOCUMENTS

| | | | |
|---|---|---|---|
| 3,658,467 A | 4/1972 | Merck ............................ 23/25 |
| 3,702,886 A | 11/1972 | Argauer ...................... 423/328 |
| 3,769,329 A | 10/1973 | Paulik ......................... 260/488 |
| 4,088,737 A | 5/1978 | Thomas et al. ............. 423/210 |
| 4,615,806 A | 10/1986 | Hilton ......................... 210/690 |
| 4,735,786 A | 4/1988 | Inque et al. ................. 423/240 |
| 4,913,850 A | 4/1990 | Puppo ......................... 252/630 |
| 5,075,084 A | 12/1991 | Wilhelm ...................... 423/241 |
| 5,139,981 A | 8/1992 | Kurland ......................... 502/11 |
| 5,155,265 A | * 10/1992 | Scates et al. ................ 562/519 |
| 5,220,058 A | 6/1993 | Fish et al. ................... 562/608 |
| 5,227,524 A | 7/1993 | Jones .......................... 562/608 |
| 5,300,685 A | 4/1994 | Scates et al. ............... 562/608 |
| 5,344,976 A | * 9/1994 | Jones et al. ................. 210/665 |
| 5,457,230 A | 10/1995 | Yang et al. .................. 562/608 |
| 5,576,458 A | * 11/1996 | Minami et al. ............. 562/519 |
| 5,801,279 A | * 9/1998 | Miura et al. ................ 562/607 |
| 5,962,735 A | * 10/1999 | Kulprathipanja et al. ... 562/606 |

* cited by examiner

*Primary Examiner*—Rosalynd Keys
(74) *Attorney, Agent, or Firm*—John G. Tolomei; Frank S. Molinaro; Arthur S. Gooding

(57) ABSTRACT

For the removal of trace quantities of iodine-containing contaminants from corrosive liquid feed streams (e.g. commercial acetic acid), an adsorbent with distinct advantages over prior-art materials is provided. The overall treatment method involves the use of a suitable zeolite having a silica to alumina molar ratio from about 5 to less than 15 that has been cation-exchanged with an iodine-reactive metal. This inorganic adsorbent may be used in unbound form, or it can be bound with a substantially insoluble porous inorganic refractory metal oxide binder. Reactivation and regeneration techniques, which are generally incompatible with prior-art adsorbent materials, are also disclosed. In general, it is advantageous to pretreat the feed streams to remove the most easily separable contaminants (e.g. iodine, hydrogen iodide, and metal cations) and thereby reduce the iodine compound loading and detrimental effects of metals on the adsorbent. Thus, the expensive iodine reactive metal (e.g. silver) used in the adsorbent preparation is judiciously used for the removal of trace quantities of iodine-containing species (e.g. alkyl iodides) that are not readily separable by other means.

36 Claims, No Drawings

COMBINATION PRETREATMENT/ADSORPTION FOR TREATING A LIQUID STREAM CONTAMINATED WITH AN IODINE-CONTAINING COMPOUND

CROSS-REFERENCE TO RELATED APPLICATIONS

This application is a continuation-in-part of U.S. application Ser. No. 09/459,100 filed on Dec. 13, 1999, now abandoned, which in turn is a continuation-in-part of U.S. application Ser. No. 09/211,791 filed on Dec. 15, 1998, now U.S. Pat. No. 6,380,428, which in turn is a continuation-in-part of co-pending U.S. application Ser. No. 09/035,798 filed on Mar. 6, 1998, now U.S. Pat. No. 5,962,735 B1 all of which are incorporated by reference.

FIELD OF THE INVENTION

The present invention relates to a novel two-step method for treating a liquid stream contaminated with an iodine-containing compound using a pretreatment step in combination with an adsorption step. The adsorption step is performed by contacting the liquid stream with a solid adsorbent material comprising a zeolite having a silica to alumina molar ratio from about 5 to less than 15 which has been cation exchanged with a metal selected from the group consisting of silver, mercury, copper, lead, thallium, palladium or mixture thereof.

BACKGROUND OF THE INVENTION

Methanol carbonylation, the reaction of methanol with carbon monoxide, is used to produce a significant share of the world's acetic acid and represents the basis for virtually all new acetic acid capacity. The fundamental process, whereby methanol and carbon monoxide are reacted in the presence of a rhodium catalyst and methyl iodide promoter, is disclosed in U.S. Pat. No. 3,769,329 B1 and has become well-known as the "Monsanto process". Although numerous improvements have since been developed, the use of an iodine-containing promoter, either as an organic iodide or metal iodide salt, has proven necessary to obtain industrially-competitive reaction rates and production economies.

Unfortunately, the use of any suitable iodine-containing promoter invariably results in the incorporation of trace iodine and organic iodide impurities into the final acetic acid product. These contaminants result from numerous transformations (thermal cracking, recombination, isomerization, etc.) of the iodine-containing catalyst promoters, which occur not only in the reactor, but also in downstream equipment, such as distillation column reboilers and recycle lines. A resulting array of $C_1$ to $C_{10}$ organic alkyl iodide species is produced, which are removed from the acetic acid product with varying degrees of effectiveness via the standard distillation steps used in down stream purification. Additionally, iodine may be present in the acetic acid product in the form of hydrogen iodide or iodide salts. Ultimately, without supplemental treatment to remove trace iodine-containing contaminants, product acetic acid made using methanol carbonylation technology with even the most careful fractionation steps, will still contain a small amount, typically below 100 parts per billion (ppb) of total iodine (both organic and inorganic) by weight.

The interest in a process for essentially complete removal of iodine-containing contaminants from acetic acid stems from the large share (about 40 to 50%) of its use as a precursor for vinyl acetate monomer (VAM) synthesis. Current methods of VAM production rely on a catalyst which is intolerant to even minute levels of iodine-containing compounds in the acetic acid feedstock. Therefore, the VAM production costs associated with reduced catalyst life increase dramatically with increasing feed iodine concentration.

Several disclosures in the prior art present techniques for the selective removal of iodine-containing species from process streams such as nuclear reactor containment environment off gases as well as emissions from spent nuclear fuel reprocessing operations. For example, U.S. Pat. No. 3,658,467 B1 addresses the removal of radioactive iodine-containing materials from the gaseous waste streams generated either during normal nuclear fuel reprocessing operations or even in the event of a fuel element cladding failure whereby radioactive methyl iodide is formed in significant amounts. The solution proposed in the '467 patent is a zeolite X molecular sieve exchanged with silver for treating the gaseous waste stream. All cited examples referring to the adsorptive ability of this formulation are based on performance in a dry air stream contaminated with trace radioactive methyl iodide. The structures of X-type zeolites are known to have aluminosilicate frameworks with maximum silica to alumina molar ratios, expressed as the ratio of $SiO_2$ to $Al_2O_3$ in the fundamental zeolite framework, of about 3 and pore openings typically in the range of 7 to 8 Å.

In U.S. Pat. No. 4,735,786 B1, an alternate solution for filtering radioactive iodine-containing compounds from nuclear facility exhaust gases in the event of an accident is proposed. In offering an improvement over the prior art, the '786 patent recognizes the practical deficiencies of silver-exchanged zeolite X adsorbent for this service under high humidity conditions. The improvement offered is a different type of adsorbent, characterized as a high silica to alumina molar ratio pentasil zeolite. The adsorbent specified is exemplified by the well-known ZSM-5 type material, which is clearly described in U.S. Pat. No. 3,702,886 B1 as having ten-member rings forming medium-sized pores in the range of 5.1 to 5.6 Å. The teachings and specific examples of the '786 patent are restricted to pentasil zeolites having silica to alumina molar ratios in the range of 15 to 100, preferably 20 to 50.

In U.S. Pat. No. 4,913,850 B1, another solution for methyl iodide removal from gaseous streams is presented, whereby a silver-exchanged "binderless" zeolite material, composed of 80 to 90% zeolite X and 10 to 20% zeolite A, is used. Among the possible candidates for zeolite X materials, those having the faujasite structure are of particular interest. As mentioned previously, zeolite X formulations generally have a maximum silica to alumina molar ratio of 3. In U.S. Pat. No. 5,075,084 B1, the progress of treating radioactive iodine-containing gas streams is continued, where the problem of the proposed silver-exchanged zeolite material catalyzing the highly exothermic reaction of hydrogen and oxygen and, in the extreme case, causing catalytic ignition of hydrogen, is solved. According to the '084 patent, this undesired side reaction is suppressed when a heavy metal such as lead is added to the silver-exchanged adsorbent. The underlying zeolite compositions of the preferred materials in this patent and the previously mentioned '850 patent are identical.

In U.S. Pat. No. 4,088,737 B1, gaseous radioactive methyl iodide removal is further addressed in a multi-step treatment procedure where the initial gas purification is performed with a silver-exchanged zeolite exemplified by zeolite X. After iodine-compound breakthrough, regeneration and concentration steps are undertaken, which involve i) withdrawing the spent adsorbent from contact with the gaseous waste stream, ii) subjecting the adsorbent to desorption conditions with a hydrogen-rich stream to produce a hydrogen iodide containing off gas, and iii) treating this effluent gas with a lead-exchanged zeolite to re-adsorb and concentrate the desorbed hydrogen iodide. Lead-exchanged zeolite X is specifically cited as achieving the desired result for the final adsorption step. The advantage of the multi-step treatment is that the long-term storage of the contaminated material is less expensive for the lead-exchanged zeolite, compared to a silver-exchanged material.

In spite of these continuing developments and improvements in trace iodine and organic iodide removal from gaseous effluent streams, the methods employed have been found unsuitable for the more difficult problem of iodine-containing compound adsorption from corrosive liquids, such as commercial acetic acid product streams. Adsorbent carrier materials of the prior art such as zeolite X and zeolite A, which are classified as having low silica to alumina molar framework ratios (typically below 5), have experimentally been proven to be unstable in acetic acid. This means that the dissolution (or leaching) rate of framework components into the liquid is sufficiently large to render such materials ineffective for iodine-containing compound adsorption service in corrosive liquid media. Depending on the specific silica to alumina framework molar ratio, the pentasil zeolites, exemplified in prior art gas-phase iodine-containing compound removal using ZSM-5, are significantly more stable in acetic acid than zeolite types X and A. However, the pore sizes of pentasil zeolites, as determined by their molecular aluminosilicate crystal channel width, are too small to effectively allow passage of the straight- and branched-chain $C_3$ to $C_8$ alkyl iodides which are generally present as contaminants in commercial acetic acid product streams. In contrast, the iodine-containing compounds present in industrial nuclear power plant waste gases are normally radioactive molecular iodine and methyl iodide only.

Other teachings more specifically apply to iodine-compound removal from corrosive liquid media, where the principal area of concern, as described previously, is in the manufacture of carboxylic acids such as acetic acid via a process which results in a product stream contaminated with trace amounts of iodine-containing byproducts. To achieve the extremely low levels of iodine-containing compounds demanded industrially, significant emphasis has been placed on the development and utilization of solid materials capable of adsorbing essentially all iodine-containing compounds from acetic acid streams.

For instance, in U.S. Pat. No. 5,457,230 B1, the use of activated carbon fiber is contemplated for this purpose. However, the examples demonstrate the removal of molecular iodine and hydrogen iodide only and fail to specifically disclose the level of iodine-containing compounds in the treated acetic acid stream. In the case of iodine-compound removal from acetic acid, it is the ability of the invention to provide a treated product with only extremely minute levels of total iodine which primarily determines its practical utility. It is known in the art that activated carbon alone can neither remove iodine-containing compounds from commercial acetic acid streams to single parts per billion levels, nor can it effectively remove organic iodide species, such as methyl iodide and hexyl iodide which are commonly present in these product streams, without the use of an iodine-reactive metal.

Recently, considerable development efforts in acetic acid purification technology have focused on resins containing iodine-reactive metals such as silver, mercury, copper, lead, thallium, palladium or combinations of these metals known to react with iodine-containing compounds to form insoluble complexes. For example, in U.S. Pat. No. 4,615,806 B1, the removal of these impurities is achieved with a macroreticulated strong acid cation-exchange resin which is stable in the organic medium and has at least one percent of its active sites converted to the silver or mercury form, presumably by cation-exchange. The use of macroreticulated resins is claimed as an advance over the prior art formulations, which are generally characterized as gel-type ion-exchange resins, for this service. In U.S. Pat. No. 5,139,981 B1, other silver-exchanged resins are offered, along with a novel technique for preparing such resin compositions. In U.S. Pat. No. 5,220,058 B1, a performance benefit is claimed, whereby the subject resin contains thiol functional groups, compared to the prior art sulfonate functional groups, which are exchanged with the iodine-reactive metal. In U.S. Pat. No. 5,227,524 B1, the resin degree of crosslinking is decreased somewhat, resulting in improved silver utilization. In U.S. Pat. No. 5,300,685 B1, the iodine-reactive metal is coordinated, as a salt, with a polymeric resin, rather than being ionically bound to a cation-exchange resin. In U.S. Pat. No. 5,344,976 B1, a resin guard bed without the iodine-reactive metal is placed upstream of the metal-exchanged resin to scavenge any metal cations in the acetic acid stream that would otherwise potentially displace the iodine-reactive metal. Finally, in U.S. Pat. No. 5,801,279 B1, an improved method of operating the iodine-compound removal step is disclosed in order to reduce the amount of leaching of the iodine-reactive metal into the treated acetic acid effluent stream. As noted in this reference, the dissolution of the iodine-reactive metal is acknowledged as a problem for iodine-compound removal techniques of the prior art whereby metal-exchanged resins are applied.

While the invention of U.S. Pat. No. 4,615,806 B1 and other modified resin-based formulations have been used commercially with some success, resins in general suffer some disadvantages, in addition to the previously-mentioned metal loss, when used in the acetic acid environment of the present invention. More specifically, resins, even those characterized as "stable" are known to "swell" or increase in diameter by as much as 50% when exposed to an organic medium, making bed design difficult. Resins are also vulnerable to decomposition at relatively mild conditions and are furthermore susceptible to chemical attack by corrosive reagents. These factors additionally complicate the use of a resin-based material for the purification of acetic acid.

Also associated with the application of resins in this service is a narrowly-limited range of acceptable operating temperatures due to decomposition, softening, loss of strength, or other detrimental structural changes resulting from thermal effects. Typically, resins begin to chemically decompose at 100 to 200° C., resulting in destruction of their fundamental networks and ion-exchange sites. For example, the preferred resin of the '806 patent is essentially a sulfonated copolymer of styrene and divinylbenzene, and at relatively mild temperatures the acid exchange sites are susceptible to acid-catalyzed desulfonation which leads to release of not only metal cations but also sulfur-containing compounds into the liquid effluent stream. Such materials interfere with further chemical processing of this product. The '806 patent is silent regarding any regeneration or reactivation method because these steps would undoubtedly require temperatures that the macroreticulated resin taught therein cannot withstand without substantial degradation.

As noted in U.S. Pat. No. 5,801,279 B1, operation of the iodine-compound removal step in an acetic acid medium at elevated temperature is beneficial in terms of improving the rate of the desired reaction, which leads to the formation of insoluble metal iodides. However, the resin-based materials traditionally employed for the treatment of acetic acid streams are generally incompatible with high-temperature operation.

A final consideration regarding cation-exchanged resins which are known in the art to adsorb trace iodine-containing compounds from liquids is the considerable expense of such materials, associated with the use of valuable iodine-reactive metals (e.g. silver or mercury) incorporated into these formulations. This concern for cost is evidenced by ongoing efforts in industry to most judiciously expend these metals by ensuring their reaction with only those iodine-containing compounds (e.g. alkyl iodides) that cannot be removed through less expensive, conventional means in a pretreatment step.

For example, in U.S. Pat. No. 5,155,265 B1, a pretreatment is offered with the intent to reduce the iodine loading on the metal exchanged resin. This method entails contacting an iodine-compound contaminated feed with ozone to oxidize the most reactive of the impurities (which also include carbonyl compounds) and thereby increase the total iodine compound removal that can be achieved using activated carbon, prior to the final treatment with a silver-exchanged resin. As noted in U.S. Pat. No. 5,457,230 B1, activated carbon alone can be useful for pretreatment purposes, based on its capacity for the adsorption of molecular iodine and hydrogen iodide. This pretreatment medium thus allows for a more selective use of metal exchange sites of the final adsorbent for the removal of only the most unreactive iodine-containing compounds. Other materials that do not comprise an iodine-reactive metal but nevertheless demonstrate a capacity for the removal for at least some iodine-containing compounds (and are thus suitable for pretreatment) include various anion exchange resins.

In U.S. Pat. No. 5,576,458 B1, a pretreatment to significantly reduce quantities of hydrogen iodide in the feed stream is disclosed, also in the context of purifying acetic acid. Most commercial acetic acid products, prior to final purification, contain hydrogen iodide in significant excess of alkyl iodides. An efficient method to remove this impurity comprises injecting methanol into the commonly used dehydration column designed for the removal of contaminant water in an overhead stream. Methanol reacts with hydrogen iodide to form methyl iodide and water, and both of these products are then separated from the acetic acid in a light fraction. Of the residual, unreacted hydrogen iodide remaining in the acetic acid, a significant portion can be further removed through subsequent reaction with a salt or base (e.g. potassium hydroxide). This step of the pretreatment results in the formation of an iodide salt (e.g. potassium iodide) which is then separated in the heavy fraction of a final distillation column, used in general in acetic acid production to separate high boiling components such as propionic acid.

Overall, the method is advantageous for removing the bulk of the hydrogen iodide and thereby preventing this component, often the most prevalent iodine-containing impurity, from quickly consuming the reactive sites of the final adsorbent. Careful consideration must be given to the amount of base added for the conversion of hydrogen iodide to iodide salt. Base injection in significant excess of the amount required to neutralize the hydrogen iodide impurity will ultimately consume acetic acid product. For example, excess potassium hydroxide will react with acetic acid to form potassium acetate salt. Of course, it is possible to employ various combinations of the aforementioned ozone treatment, adsorption, distillation, methanol injection, and neutralization steps for pretreatment of a liquid stream contaminated with an iodine-containing compound.

An alternative type of pretreatment involves the removal of contaminant metals in the form of metal cations that are also normally present in the iodine contaminated feed stream of the present invention. These metals originate mainly from the metallic catalysts and catalyst promoters used in upstream conversion (e.g. methanol carbonylation) operations. Metals are also present to some extent due to the corrosion of materials used for the production plant.

Thus far, therefore, the prior art has offered several techniques for the removal of both iodine-containing impurities and contaminant metals. These methods, while they fail in isolation or in combination to achieve the extremely low levels of iodine-containing compounds demanded industrially, are valuable in many cases for pretreatment to remove particular contaminants prior to a final adsorption step. Thus, the efficiency of the adsorbent used in this step is maximized in terms of separating only the most non-reactive iodine-containing compounds, which are usually present in very small quantities. Nevertheless, regardless of the pretreatment, the effectiveness of the treating method overall is dependent on the performance of the final adsorbent for removing trace impurities such as methyl and hexyl iodide to single ppb levels or below. It is understood hereafter that trace iodine contamination levels are expressed in terms of the total weight of iodine relative to the weight of the liquid stream in which iodine contaminants are present.

The problem therefore addressed by the present invention is to provide a method comprising both a pretreatment and an adsorption step for the essentially complete removal of iodine-containing impurities from liquids such as commercial acetic acid product streams. At least a portion of these impurities, or at least a portion of a metal contaminant, is removed in the pretreatment step, while at least a portion of the residual iodine-containing compounds not removed in this step are subsequently adsorbed in the adsorption step. The invention is further characterized in that the adsorbent used in the final adsorption step is free of the substantial temperature restrictions, chemical exposure effects, and swelling problems associated with the typical organic resin materials used in the prior art. Another feature of the adsorbent is that it may be conveniently reactivated by contacting it with a solution of iodine-reactive metal cations when the originally loaded metal becomes deactivated after reaction with iodine-containing impurities.

Furthermore, because the adsorbent can be subjected, without any undue performance deficit, to a significantly wider range of conditions than those of the prior art, the invention also provides a means for adsorbent regeneration through contact with a regenerant gas stream at elevated temperature. Such a regeneration is described in detail in U.S. Pat. No. 4,088,737 B1 for zeolite-based adsorbents used in the well-known process of iodine-containing compound removal from gas streams. The regeneration entails subjecting the spent adsorbent to a stream of hot gas comprising hydrogen.

Significant teachings in the prior art associated with the use of non-resin adsorbents actually point away from their utility in the treatment of corrosive liquid media. In particular, in the comparative example recited in U.S. Pat. No. 4,615,806 B1 (column 6, lines 36 to 49), a silver-exchanged zeolite, characterized as $1/16$ inch 5A molecular sieve pellets, was tested in acetic acid for contaminant methyl iodide removal and found to be unstable as evidenced by the continuous silver leaching from the adsorbent and the finding of a yellowish precipitate in the treated effluent. Given this discouraging result, it is remarkable that a suitable inorganic adsorbent for use in this corrosive environment has been discovered.

The adsorbent material in fact comprises a zeolite that has been cation exchanged with a metal known to react with iodine-containing compounds, present in trace amounts in the feed stream of the present invention. This finding of an inorganic material suitable for the treatment of a corrosive acetic acid feed stream is associated with the realization that zeolites with sufficiently high silica to alumina molar ratios are indeed stable in this service. The silica to alumina molar ratio, of course, refers to the composition of the fundamental three dimensional network structure which characterizes the zeolite. It is actually this variable, rather than the type of zeolite itself, which determines its ability to withstand corrosive liquid environments. Experimentally, good results were obtained with silica to alumina molar ratios above about 5, with better results obtained at ratios above about 6.5, and superior results obtained at ratios above about 8. The upper bound of the silica to alumina molar ratio is based on the amount of ion exchange sites available for loading of a suitable iodine-reactive metal (e.g. silver). In contrast to the teachings of the aforementioned U.S. Pat. No. 4,735,786 B1, zeolites having silica to alumina molar ratios of less than 15 are in fact useful for iodine-compound removal. Such zeolites have been found sufficiently stable in acidic media and also in possession of adequate ion exchange capacity for effective contaminant removal to parts per billion levels.

A further unexpected finding was that such a silica-rich zeolite, when used in iodine-containing compound adsorption service of the present invention, can be reactivated using a relatively simple procedure and also regenerated at high temperatures when necessary.

SUMMARY OF THE INVENTION

In one embodiment the present invention is a process for treating a liquid feed stream containing a contaminant comprising an iodine compound, the process comprising 1) pretreating the liquid feed stream to remove at least a portion of the contaminant and yield a pretreated liquid feed stream containing at least a residual amount of the iodine compound, and 2) contacting the pretreated liquid feed stream with an adsorbent comprising a zeolite having a silica to alumina molar ratio from about 5 to less than 15 which has been cation exchanged with a metal selected from the group consisting of silver, mercury, copper, lead, thallium, palladium, and mixtures thereof, at adsorption conditions to adsorb at least a portion of residual amount of iodine-compound to yield a treated liquid stream.

In a more specific embodiment the pretreating step of the present invention as described above comprises 1) contacting the liquid feed stream with methanol to convert at least a portion of the iodine compound to methyl iodide and yield a methyl iodide-containing liquid stream, 2) fractionating the methyl iodide-containing liquid stream to separate at least a portion of the methyl iodide therefrom in an overhead liquid stream and yield a bottoms liquid product stream containing at least a portion of the iodine compound, 3) contacting the bottoms liquid product stream with a salt or a hydroxide compound of a cation to convert at least a portion of the iodine compound therein to an iodide salt and thereby yielding an iodide salt-containing liquid stream, 4) fractionating the iodide salt-containing liquid stream to separate at least a portion of the iodide salt therefrom in a heavy ends liquid stream and yield a light ends liquid product stream, and 5) contacting the light ends liquid product stream with a pretreatment medium to provide the pretreated liquid stream.

A secondary object of the present invention is to provide the process as described above, where the process is carried out until the adsorbent has substantially reached its adsorption capacity, at which point the adsorbent is reactivated by contacting it with a solution of a salt of a reactivation metal where the metal is selected from the group consisting of silver, mercury, copper, lead, thallium, palladium, and mixtures thereof such that an amount of reactivation metal is added to the adsorbent.

Still another object of the present invention is to provide the process as described above, where the process is carried out until the adsorbent has substantially reached its adsorption capacity, at which point the adsorbent is contacted with a regenerant gas stream comprising hydrogen at conditions effective to strip substantially all of the adsorbed iodine as hydrogen iodide to yield a regenerated adsorbent.

Other objectives and embodiments are associated with the various preferred procedures and features connected with the invention and are discussed in the following detailed description.

DETAILED DESCRIPTION OF THE INVENTION

The feed for the process of the present invention can be broadly any liquid stream contaminated with one or more iodine-containing compounds. Typically, such feeds are produced in industrial processes that require the use of iodine-containing compounds to promote or catalyze the desired synthesis reaction. Well-documented examples of such reactions include the oxydehydrogenation of various inorganic materials to make the corresponding unsaturated compounds. Of utmost concern to the present invention, however, is the use of organic and inorganic iodine-containing promoters in the catalytic carbonylation of alcohols to yield the corresponding carboxylic acid.

In the specific case of modern methanol carbonylation technology, the iodine-containing promoter is typically methyl iodide, lithium iodide, hydrogen iodide, or, more likely, some combination of these components. The acetic acid produced, however, will normally contain a broader range of iodine-containing compounds, including traces of $C_1$ to $C_{10}$ linear and branched organic iodides as well as inorganic iodide salts of lithium and other cations either used to catalyze the reaction, formed from corrosion of the plant metallurgy, or introduced in downstream purification operations. This large variety of possible iodine-containing compounds results from the "scrambling" or recombination and rearrangement reactions of iodine-containing compounds, initially introduced as promoters, in recycle lines and processing equipment.

Normally, however, multiple distillation steps downstream of the reactor are used to separate the desired acetic acid product from unconverted reactants, catalyst promoters, and byproducts from both equilibrium and irreversible reactions. As a result of these purification measures, the predominant alkyl iodide species contaminating the acetic acid product and thus the feed stream to the present invention, are hydrogen iodide and $C_1$ to $C_8$ alkyl iodides. Also included in this feed stream are a small amount of water, generally limited to about 2000 parts per million (ppm) by weight, and trace amounts of byproduct aldehydes, alkanes, ketones, and carboxylic acids heavier than acetic acid which together normally account for less than about 500 ppm by weight of the total acetic acid stream. These other impurities do not significantly affect the ability of the adsorbent of the present invention to remove the iodine-containing compounds. The presence of metal contaminants, however, can diminish the adsorption performance through ion exchange of such contaminants with the reactive metal used in the adsorbent.

The preferred iodine-reactive metals used in the adsorbent preparation are very effective for removing even trace quantities of a broad range of iodine-containing compounds. This is because substantially insoluble metal iodide compounds are formed by the reaction of iodine, hydrogen iodide, metal iodides, and organic iodides in the feed stream with an appropriate reactive metal, selected from the group consisting of silver, mercury, copper, lead, thallium, palladium, and mixtures thereof. As understood in the art, the nature of the metal iodide formed is dependent upon the type of iodide reactive metal employed but not the particular iodine-containing compound in the feed stream.

While the adsorbent is therefore extremely selective for adsorbing iodine-containing impurities, the metallic ingredient used therein is generally expensive. For this reason, a number of pretreatment steps known in the art to remove either specific iodine compounds or metals from the iodine-compound containing liquid stream can provide a more economically attractive process for the essentially complete removal (i.e. to less than 10 ppb expressed as total iodine) of iodine contaminants than the use of the adsorbent of the present invention alone. For example, pretreatment of the contaminated liquid stream to remove specific iodine-containing impurities (i.e. iodine and hydrogen iodide) prior to the subsequent treatment with the adsorbent of the present invention provides for judicious use of the iodine-reactive metal.

Otherwise, a pretreatment directed to the removal of metal contaminants will prevent the loss of valuable iodine-reactive metal used in the adsorbent formulation through ion exchange of contaminant metal with iodine reactive metal. Thus, the removal of metal contaminants prior to adsorption will effectively extend the adsorbent life compared to the case where this pretreatment step is absent. Overall, then, a pretreatment step prior to adsorption is effective when either of the following are removed: 1) reactive iodine-containing impurities, which can be removed largely by conventional means and, if allowed to pass to adsorbent of the present invention, would quickly expend its valuable iodine-reactive metal sites, or 2) metals, which, in their cationic form in solution, could deplete the iodine-reactive metal sites of the adsorbent through ion exchange. The removal of either iodine-compounds or metals can be accomplished by any of several methods described herein or combinations thereof. It is important to recognize, however, that the overall effectiveness of the process of the present invention depends on the use of the novel cation exchanged zeolite adsorbent, which has been heretofore unknown in the art, for the final adsorption step. If an appropriate pretreatment step is incorporated for the removal of iodine-containing compounds, the adsorption step could then entail, for example, reducing the total iodine in the feed stream from about 10–1000 ppb to less than 10 ppb by weight.

In general, then, the process of the present invention for treating a liquid stream contaminated with an iodine compound comprises both a pretreatment and an is adsorption step. The pretreatment step is effective for removing at least a portion of either contaminant iodine compound, contaminant metal, or both, to provide a pretreated liquid feed stream containing at least a residual amount of the iodine compound. If the pretreatment step is intended to remove metals only, then substantially all of the iodine compound present initially in the liquid feed stream may also be contained in the pretreated liquid feed. If, however, the liquid feed stream contains primarily hydrogen iodide and molecular iodine, appropriate means for pretreatment for the removal of these iodine compounds may significantly reduce the total iodine content of the pretreated liquid feed. In any case, the adsorption step following the pretreatment step removes additionally at least a portion of the residual amount of the iodine compound contained in the pretreated liquid feed. Thus, the combination of pretreatment and adsorption may be used to provide a treated liquid stream wherein substantially all of the iodine-containing compounds have been removed.

It is recognized, then, that an optional pretreatment within the scope of the present invention is described in U.S. Pat. No. 4,615,806 B1 where a carbonaceous material is used specifically to remove hydrogen iodide and molecular iodine prior to the iodine-containing compound adsorption treatment step. Particularly effective in this service are carbonaceous materials including activated carbons, wood charcoal, bone char, lignite, and others which may be impregnated with alkali metals known to increase the inorganic iodine compound chemisorption capacity. Of these carbonaceous materials, activated carbon and, as noted in aforementioned U.S. Pat. No. 5,457,230 B1, hereby incorporated by reference, activated carbon fiber are both preferred forms. Also particularly effective for removing hydrogen iodide are various anion exchange resins, such as Reillex® 425, a crosslinked polyvinylpyridine (available from Reilly Industries, Indianapolis, Ind. USA), Deloxan® THP (available from Degussa AG, Frankfurt, Germany), or Amberlite® IRA-958 (available from Rohm and Haas Company, Philadelphia, Pa., USA).

Another pretreatment option, as mentioned previously, is disclosed in U.S. Pat. No. 5,344,976 B1, whereby a cation exchange resin guard bed without any iodine-reactive metal is placed upstream of the iodine-containing compound removal adsorbent of the present invention to scavenge any metal cations, thus preventing their exposure to the adsorbent. As is known to commercial producers of acetic acid, metal cation contamination of the product can stem from reaction catalysts and co-catalysts and corrosion of the plant metallurgy. Metal contaminants are normally present as cations and, depending on the specific process and plant construction materials, are often one or more of the following: $Rh^{+3}$, $Ir^{+3}$, $Ru^{+3}$, $Os^{+3}$, $Re^{+5}$, $Co^{+2}$, $Ni^{+2}$, $Mo^{+5}$, $V^{+3}$, $Fe^{+3}$, $Ti^{+4}$, and $Zr^{+4}$. To effectively remove undesired metal cations which could otherwise potentially displace the iodine-reactive metal of the adsorbent of the present invention, a number of strong acid cation exchange resins are suitable, normally used in their hydrogen form. Such resins include Amberlyst® 15 (available from Rohm and Haas Company, Philadelphia, Pa., USA) and others, as described in the '976 patent. Depending on the specific characteristics of the iodine contaminated feed stream, the use of either a guard bed of carbonaceous material, cation exchange resin, or both may prove beneficial for improving the efficiency and/or extending the practical life of the reactive metal containing adsorbent.

The present invention, in contrast to the prior art, recognizes the utility and advantages of employing a zeolite-based adsorbent for the treatment of an iodine-compound containing liquid stream. Therefore, the non-metal exchanged form of a zeolite of the same type used for the cation-exchanged zeolitic adsorbent of the present invention, may be incorporated upstream of this adsorbent as a scavenger of metals and other impurities. Overall, then, appropriate pretreatment media for use prior to the adsorbent of the present invention comprise the non-metal exchanged form of the zeolite used in the adsorption step, resins, and activated carbon. These materials are all potentially effective for reducing the loading of iodine compounds or metallic contaminants to the final adsorption step comprising contacting the liquid feed stream with a cation-exchanged zeolite. Furthermore, depending on the contaminant types and levels in the liquid feed stream, it may be desirable to combine two or more of the above mentioned pretreatment media in a single bed upstream of the cation exchanged zeolitic adsorbent. Multiple beds of pretreatment media can, of course, also be employed.

An alternative pretreatment step is taught in U.S. Pat. No. 5,576,458 B1, hereby incorporated by reference. In this disclosure, the effectiveness of commercial acetic acid fractionation operations can be improved by adding methanol to a distillation column, located downstream of the carbonylation reactor, where the column is typically employed to separate water and other low-boiling components (e.g. methyl iodide). Methanol in this environment reacts spontaneously with hydrogen iodide, which is not easily separable from acetic acid using standard fractionation, to form methyl iodide and water. Both the water and methyl iodide reaction products are then removed in the overhead of the column, which is normally referred to as the drying or dehydration tower. Thus, the feed stream of the present invention can be contacted with methanol in a pretreatment step to convert at least a portion of the iodine compound to methyl iodide and yield a methyl iodide-containing liquid stream. This stream can then be fractionated to separate at least a portion of the methyl iodide therefrom in an overhead liquid stream to provide the pretreated liquid stream of the present invention. This pretreated liquid stream, or the bottoms liquid product stream of the fractionation, can also be further contacted with any of the aforementioned pretreatment media to provide the pretreated liquid stream of the present invention.

Methanol injection combined with distillation is taught to reduce the total iodine content of the acetic acid, in a typical methanol carbonylation operation, from the order of thousands to the order of hundreds of ppb by weight. Thus, this practice is also an appropriate pretreatment step in the method of the present invention. It is understood that fractionation as it applies here can also include a single stage of distillation, commonly referred to as a flash operation.

Additionally, a significant portion of the remaining, unreacted hydrogen iodide can be further removed through first contacting the impure acetic acid stream with a solution of a salt or of a hydroxide compound, or mixture thereof, with or without hypophosphorous acid. In this case, salt compounds refer to halide, nitrate, sulfate, or phosphate compounds of a metal cation or of $NH_4^+$. Preferably, the salt or hydroxide compound used in this conversion step comprises a cation selected from the group consisting of $Na^+$, $Li^+$, $K^+$, $Mg^{+2}$, $Ca^{+2}$, and $NH_4^+$. The addition of such salt or hydroxide converts or neutralizes most of the residual hydrogen iodide to form an iodide salt. For example, if potassium hydroxide is added to a crude acetic acid product some potassium iodide is produced.

Thus, a pretreating step of the present invention involves contacting the liquid feed stream with a salt or a hydroxide compound of a cation to convert at least a portion of the iodine compound to an iodide salt and thereby yield an iodide salt-containing liquid stream. This stream can then be fractionated to separate at least a portion of the iodide salt therefrom in a heavy ends liquid stream and provide the pretreated liquid feed stream. This resulting pretreated liquid stream, which is effectively the light ends liquid product stream from the fractionation, can also be further contacted with any of the aforementioned pretreatment media to provide the pretreated liquid stream of the present invention.

This conversion of hydrogen iodide to an iodide salt is desirable because the salt can be essentially completely removed by boiling the acetic acid into an overhead stream while retaining the salt and other less volatile impurities in a bottoms fraction. Conveniently, it is normal practice in commercial acetic acid production to incorporate a distillation column, commonly referred to as a heavy ends tower, for separating high-boiling impurities (e.g. propionic acid), downstream of the dehydration tower. When combined with the previously mentioned methanol injection and distillation procedure, the contacting of acetic acid with a salt or hydroxide solution, coupled with distillation, is known to further reduce hydrogen iodide levels in commercial crude acetic acid streams from the order of hundreds of ppb to less than 100 ppb. This method, comprising contacting the liquid feed stream with a salt or hydroxide solution followed by distillation, therefore is an acceptable pretreatment useful for the method of the present invention. Of course, a simple flash operation (i.e. a single stage of distillation) may be used to separate iodide salts in place of the multiple stage fractionation typically used in commercial heavy ends removal. As stated, it is also possible to combine the aforementioned methanol injection/fractionation procedure with the base or salt injection/fractionation procedure and also potentially with the pretreatment medium contacting procedure to provide an overall pretreatment step comprising several individual procedures.

Prior to contacting the iodine-compound contaminated acetic acid feed stream with the adsorbent of the present invention, pretreatment steps other than 1) contact with a pretreatment medium or 2) methanol injection and fractionation (or possibly flash vaporization) may likewise be suitable. For instance, another possible pretreatment to reduce feed stream iodine-containing compound levels prior to the adsorptive method of the present invention is described in U.S. Pat. No. 5,155,265 B1, hereby incorporated by reference. Specifically, the contacting of a contaminated commercial acetic acid stream with ozone is taught to be beneficial for oxidizing not only organic iodides but also carbonyl impurities that can negatively impact the product permanganate time, an important specification that is known to acetic acid producers. These carbonyl contaminants (e.g. crotonaldehyde) are of particular concern when the acetic acid is produced according to a so-called "low water" process where high reaction rates are achieved by maintaining a low water concentration in the reaction mixture while concurrently introducing a significant amount of iodide salt (e.g. lithium iodide).

Regardless of the production method used, however, the pretreatment of iodine-compound contaminated acetic acid with ozone can convert at least some of the hydrogen iodide and alkyl iodides to species (i.e. molecular iodine) that can be removed by subsequent adsorption onto a resin or activated carbon. Therefore, the contacting of the liquid feed stream of the present invention with ozone to yield an ozonated liquid stream followed by contacting this ozonated stream with a pretreatment medium can also provide a pretreated liquid stream.

Of course, depending on the nature of the liquid feed stream contaminants, various combinations of the steps and procedures described herein may also be used effectively as a single pretreatment to reduce the total iodine level of the feed stream significantly prior to contact with the metal-exchanged adsorbent of the present invention. For example, the methanol injection/distillation method may be followed by contacting the liquid with a hydroxide or salt in combination with a second distillation as described in the previously mentioned U.S. Pat. No. 5,576,458 B1. Alternatively, the reaction of the contaminated liquid feed with a hydroxide or salt, combined with distillation, may be performed without the prior methanol injection and distillation. Furthermore, a pretreatment medium as described previously may be incorporated between any of the aforementioned pretreatment steps (i.e. methanol injection, ozonation, contact with a hydroxide or salt) and the final adsorptive treatment step using a metal exchanged, zeolite containing adsorbent.

Within the scope of the present invention, it is also possible to distill or fractionate the treated liquid stream, or effluent from the cation-exchanged zeolitic adsorbent in order to remove trace quantities of iodine-reactive metals or metal oxide components of the zeolite that may leach from the adsorbent during the adsorption step. This final distillation will therefore provide a liquid product essentially free of components present in the adsorbent (e.g. silica). Conveniently, such a purification is possible in the commercial manufacture of acetic acid via methanol carbonylation if the adsorbent is incorporated in the process flow prior to the aforementioned heavy ends tower. Again, in place of distillation, a single stage flash vaporization can also be utilized, as this operation is considered here as a special case of distillative separation.

In the adsorption step following the pretreatment step of present invention, the novel adsorbent used to treat the pretreated liquid feed contaminated with at least a residual amount of an iodine compound comprises a zeolite that has been cation exchanged with a metal that is reactive with iodine and iodine-containing compounds. The adsorbent is typically in a pellet, pill, or extrudate form. Furthermore, the distinguishing and novel characteristics of the zeolite are its silica to alumina framework ratio and pore size, both of which are particularly important to the overall effectiveness of the material for use in treating corrosive liquid streams. As explained previously, the silica to alumina molar ratio of the zeolite must allow for sufficient stability in corrosive environments. A simple test to determine whether the silica content of the zeolite is sufficient comprises subjecting it to a solution of pure acetic acid at a temperature corresponding to the proposed operating temperature, preferably from about 30° C. to about 150° C., for 24 hours. Any substantial dissolution of the framework alumina appears as a cloudy precipitate in the liquid. Another practical consideration for determining the optimal silica to alumina molar ratio of the zeolite is that the amount of available exchange sites for loading the iodine-compound reactive metal directionally decreases with increasing silica content. Therefore, zeolites with excessive silica to alumina molar ratios (greater than about 15) are not recommended. The effective range of the silica to alumina molar ratio for the zeolitic adsorbent of the present invention is from about 5 to less than 15. Preferably, this ratio is from about 8 to about 12. It is important at this point to distinguish the silica to alumina ratio (or $SiO_2/Al_2O_3$ ratio) from another commonly-used term in the art, the "Si/Al ratio", which is exactly half of the silica to alumina molar ratio.

For adsorption activity, three broad zeolite classifications exist and are described as having 8-, 10-, or 12-member rings according to the number of tetrahedral molecule building blocks linked together in the zeolite structure. In the present invention, the preferred zeolites are those of large-pore consideration, whose molecular sieve channels are formed by 12-member rings. Such large-pore zeolites, with channel aperture widths of greater than about 6 Å, allow for fast diffusion of even the high molecular weight and branched alkyl iodide compounds, known to contaminate the pretreated liquid feed stream, to the iodine-reactive metal-exchanged sites. Useful zeolites within the 12-member ring classification are mordenite, zeolite Y, zeolite L, omega, ZSM-12 and beta. The type Y zeolites in this case are broadly defined and described according to synthesis procedures and structural details in U.S. Pat. No. 3,130,007 B1 which is incorporated by reference. Zeolites L, omega, ZSM-12, and beta are defined and described according to synthesis procedures and unique structural details in U.S. Pat. Nos. 3,216,789 B1, 4,241,036 B1, 3,832,449 B1, and 3,308,069 B1, respectively, all of which are incorporated by reference. Useful zeolites within the 10-member ring classification are ZSM-5, defined in U.S. Pat. No. 3,702,886 B1, incorporated by reference; ZSM-11, defined in U.S. Pat. No. 3,709,979 B1, incorporated by reference; ZSM-23, defined in U.S. Pat. No. 4,076,842 B1, incorporated by reference; some of the silicalite materials, defined in U.S. Pat. No. 4,061,724 B1, incorporated by reference; and ferrierite.

Mordenite is a naturally-occurring siliceous zeolite that is available as either an 8-member or 12-member ring structure. It is the 12-member ring structure, known as "large port" mordenite or "zeolon", which is most applicable to the present invention. The structure, composition, properties, and method of synthesis of mordenite zeolite are described in *Zeolite Molecular Sieves* by Donald W. Breck (John Wiley and Sons, 1974) at pages 122 to 124 and 162 to 163 which may be consulted for further details.

Zeolites having the Y structure, modified to achieve a specific range of silica to alumina framework ratios mentioned previously, are also of primary interest to the present invention. Particularly preferred are Y zeolites modified either by steam stabilization, chemical treatment, or a combination of these procedures. Steam stabilization of a Y zeolite normally involves calcination of its ammonia or hydrogen form starting material at relatively high temperatures (above about 500° C.) in the presence of steam. Typically, this procedure is followed by additional ammonia ion-exchange procedures and subsequent steam calcination treatments until the sodium content of the resulting zeolite is below 0.5% by weight, calculated as sodium oxide. U.S. Pat. No. 3,929,672 B1, which is incorporated by reference, contains additional details concerning a preferred steam-stabilized Y zeolite useful in the present invention.

Another type of modified Y zeolite of interest in this case is the LZ-210 version that requires chemical treatment to increase its silica to alumina framework ratio through "secondary synthesis" technology. A definition of zeolite LZ-210 and details of its synthesis from conventional Y zeolite by chemical treatment is given in U.S. Pat. No. 4,503,023 B1, which is incorporated by reference. The last type of modified Y zeolite particularly useful in the present invention is characterized as Y-85, which is a steam-stabilized and chemically-modified zeolite Y. Preparation details for Y-85 are fully disclosed in U.S. Pat. No. 5,013,699 B1, which is incorporated by reference. Experimentally, however, of the Y zeolites, it has been found that the best practice is to use LZ-210 type materials that have molar silica to alumina framework ratios as defined previously. LZ-210 zeolite is thus a particular type of hydrophobic, large-pore, zeolitic material that is suitable for use in the adsorbent of the present invention.

The zeolitic molecular sieve adsorbent used in the adsorption step of the present invention is activated by suitable ion exchange with any metal known to be reactive with iodine-containing compounds. Particularly, ion exchange with silver, mercury, copper, lead, thallium, palladium or mixtures thereof gives good results for use in liquid-phase iodine compound adsorption service. It is well known that, for converting the sodium, ammonia, or hydrogen form of the molecular sieve starting material into the metal-exchanged form suitable for use in the present invention, any water soluble salt of the metals recited above is appropriate as an ion-exchange medium. Also, a non-aqueous organic medium may be used provided sufficient solubility of the salt is possible. Acetate, nitrate, or halide salts are ordinarily used for the ion-exchange procedure and the appropriate conditions are typically room temperature and atmospheric pressure. The contact of cation-rich solutions with the zeolite-containing molecular sieve can be repeated to obtain a desired metal loading. In some cases, drying and calcining the material between ion-exchange treatments may improve penetration of the metal into the zeolite molecular sieve material. After completion of the ion-exchange step, it is necessary to dry the ion-exchanged material at about 100° C. to about 200° C. for several hours to remove any residual solution and activate the zeolite.

For use in the adsorbent of the present invention, the most preferred metal for ion exchange is silver, with best results achieved when the silver loaded represents about 1% to about 15%, preferably about 8% to about 14% on an elemental basis, of the dried adsorbent weight. Where the zeolite is available only in a powder form, it is often desired to bind this fine material into larger particles such as pellets, extrudates, or spheres. For such cases, the ion-exchange procedure can be applied directly to the zeolite powder prior to binding. Alternatively, the preferred procedure is incorporation of the metallic cation into the zeolite after binding it into a particle suitable for a commercial packed-bed system. Typically, the crystal size of molecular sieve powder is 0.1 to 6 microns but the crystallites are agglomerated into particles of 10 to 20 microns in diameter. In contrast, particles useful for fixed-bed applications have diameters of about 1600 microns, although their exact size is not critical, provided the bed pressure drop is acceptable in commercial operation. It is to be noted that mordenite zeolite powder alone may be formed into various shapes large enough so that, for the practical purposes of the present invention, a separate binding agent may not be necessary.

In the prior art, there are many ways described for combining a binder material with molecular sieves to make larger size particles with sufficient strength suitable for use in the adsorption step of the present invention. It is of course, necessary that the binder material is not soluble to any significant degree in the corrosive liquid feed stream to be treated. The test for the appropriate degree of insolubility is a finding of below about 10 ppm of the binder material in the treated feed stream effluent of the present invention under iodine-compound adsorption conditions after 100 hours. The initial 100 hours provides a reasonable period for the adsorbent to stabilize and reach its start-of-run composition. Binder materials found to satisfy the substantial insolubility requirement and exhibit utility in preparing the adsorbent of the present invention are the inorganic refractory metal oxides selected from the group consisting of silica, titania, zirconia, chromia, boria, vanadia, magnesia, and mixtures thereof. Preferred binder materials are selected from the group consisting of silica, titania, zirconia, and mixtures thereof. Silica, in addition to its stability in corrosive media, is most preferred in practice because of its ready availability and low cost. Binder materials such as alumina which are susceptible to attack in acidic solutions are not suitable.

If it is determined that shaped agglomerates of the zeolitic molecular sieve and binder material are to be formed, an extrusion procedure is incorporated where the zeolite and binder are first blended in the proper ratio. The resulting mixture is combined with water and a peptizing agent to form a gel or dough that is then extruded into pellets most commonly having a circular cross section. The union of the binder and zeolite material can also result in the formation of spherical beads, using technology well-known in the adsorbent art. It is certainly possible to form other cross sectional shapes; the main objective is to reduce the gross diffusional path of iodine-containing contaminants in the pretreated liquid feed stream into the adsorbent pores.

If spherical adsorbent agglomerates are desired, the preferred method of forming is according to the well-known "oil-dropping" technique. This procedure essentially involves the initial synthesis of an appropriate sol, or carrier material, of the binder used for suspending the active zeolitic material. Details of this technique are provided in U.S. Pat. No. 2,620,314 B1, which is incorporated by reference. In the case of the preferred binders mentioned for producing the adsorbent material of the present invention, it is appropriate to make an acidic hydrosol that can be gelled using the type of temperature-activated gelling agent set forth in the '314 patent. The preferred temperature-activated gelling agent is hexamethylenetetramine (HMT). It is also recognized that in some cases silica sols may gel without a gelling agent or even a substantial change in temperature. This type of sphere formation is also within the scope of the present invention. Types of silica sols used to form the silica binder are commercially available as aquasols or organosols containing dispersed colloidal silica particles.

For performing oil dropping with a silica sol, an inverted silica sol, produced by an acid addition technique and a basic gelling agent such as a mixture of urea and HMT, is preferred. When a zirconia binder is used for the adsorbent preparation, the preferred acidic sol is an aqueous zirconyl hydroxylchloride and urea solution. When a titania binder is used, the acidic sol is preferably a solution of titanyl oxychloride and urea.

The important feature of the technique for forming agglomerates is to avoid any significant binder blockage of molecular sieve pores by the sol. In the case of the present invention, this phenomenon, called "binder blinding", would cause binder interference with access of the iodine-containing compounds to the active sites in the molecular sieve. To overcome this effect, it may be necessary to add an inert diluent, typically of somewhat smaller size than the zeolite powder, to the mixture of zeolite and binder prior to agglomerate formation. This diluent can act as a bridging material for the binder and molecular sieve, thus preserving the zeolite pore system. Typical inert diluents used to prevent binder blinding are non-colloidal silica and some types of clays resistant to low pH conditions. An essential feature of the present invention, of course, is that the chemical characteristics of the binder are properly matched with those of the zeolite, if such a bound zeolitic material is in fact used. Regardless of the method of agglomerate formation, the resulting particles should be dried at about 80° C. to about 150° C. for several hours and then calcined in dry air.

Typically, the initial forming stage in the production of extrudates, beads, pellets, or other shapes yields "green" particles which possess sufficient strength for a subsequent calcination step to set the binder and activate the molecular sieve. The temperatures most commonly used for this calcination or firing step range from about 450° C. to about 700° C., preferably about 600° C. to about 650° C. The binder is typically present in the in an amount of less than about 30% by weight, preferably between about 15% and about 25% by weight of the binder and zeolite combined. Therefore, where a bound cation-exchanged zeolite is used for the adsorbent of the present invention, the zeolite should comprise at least about 70%, and preferably from about 75% to about 85% of the adsorbent weight, not considering the weight of the cation-exchange metal ("metal-free" basis).

According to the present invention, the pretreated liquid feed stream contaminated with iodine-containing compounds is contacted with an adsorbent comprising a zeolite exchanged with metallic cations, which are reactive with the iodine-containing impurities. A binder material may or may not be necessary, depending on the type of zeolite used. Of the zeolite materials mentioned previously which are most preferred for the adsorbent of the present invention, mordenite does not necessarily require the use of a porous refractory inorganic oxide binder.

The adsorption conditions used in the adsorption step of the present invention include an absolute pressure at least sufficient to maintain the feed stream as a liquid. In most cases, this absolute operating pressure is about 0.5 to about 10 atmospheres (about 51 to about 1010 kPa), preferably about 1 to about 5 atmospheres (about 101 to about 505 kPa) at a temperature of about 20° C. to about 350° C., preferably about 30° C. to about 150° C. In general, higher temperatures improve the interaction of the iodine-containing contaminants with the reactive metal that is deposited onto the adsorbent and thereby increase the utilization of the reactive metal sites. It is also noted that the adsorbent of the present invention can successfully withstand considerably higher temperatures than the resin-based adsorbent formulations of the prior art. A suitable liquid hourly space velocity (LHSV) is in the range from about 0.1 to about 15 $hr^{-1}$, preferably about 1 to about 10 $hr^{-1}$. As understood in the art, the LHSV is the hourly volumetric liquid flow rate divided by the adsorbent volume and represents the reciprocal of the average time of the liquid within the adsorbent bed.

After an extended period of operation in pretreated liquid iodine-compound removal service the reactive metal is gradually converted to its metal iodide, while the zeolite ion-exchange sites are concurrently changed to their hydrogen form. Electron microscopy analysis of silver-loaded zeolitic adsorbents after use has indicated a migration of silver iodide molecules and subsequent agglomeration at various points on the outer surface of the adsorbent. As substantially all of the iodine-reactive metal is converted to metal iodide, the adsorbent gradually loses its effectiveness, so that the treated liquid stream may no longer conform to the product quality specifications demanded in terms of total iodine content. At this point, the adsorbent has substantially reached is adsorption capacity and a simple metal exchange procedure can restore activity.

The technique requires subjecting the adsorbent, either in situ or ex situ, to a solution of iodine-reactive metal cations, preferably the same type of solution used originally for the cation-exchange procedure. The ion-exchange treatment introduces an additional portion of the active metal, thereby re-establishing the metal-exchanged zeolite sites active for iodine-containing compound adsorption. Thus, the adsorbent activity for iodine-compound removal is restored. The amount of metal added in this reactivation treatment is preferably about 0.5 to about 1.5 time the amount originally deposited onto the carrier, with the specific quantity determined by the extent of deactivation of the adsorbent activity. The reactivation procedure can be repeated multiple times to vastly extend the adsorbent life, until the active zeolite metal-exchange sites become obstructed with silver iodide to such an extent that more severe treatment steps are necessary to restore the iodine-containing compound adsorption capacity.

When the reactivation procedure fails to reestablish sufficient iodide removal capacity of the spent adsorbent, it is possible to free the molecular sieve pores of the iodine-containing compounds adsorbed during iodide removal service. A beneficial regeneration step involves exposure of the spent adsorbent to a high-temperature hydrogen-containing gas stream. Of course, as is common in industrial hydrogen streams, the gas used in the regeneration step may comprise a mixture of hydrogen and a diluent gas selected from the group consisting of nitrogen, argon, methane, ethane, propane, and mixtures thereof. This treatment has proven to reduce silver to its elemental form and simultaneously liberate hydrogen iodide. As is explained in U.S. Pat No. 4,088,737 B1, this regeneration procedure requires a moderate absolute pressure of about 1 to about 10 atmospheres (about 101 to about 1010 kPa), a high temperature of about 400° C. to about 550° C., and a gas hourly space velocity (GHSV) of about 400 to about 1000 $hr^{-1}$. This treatment generates a gas stream containing hydrogen iodide that can be either neutralized or re-adsorbed onto a cheaper adsorbent for long-term storage.

Once the iodine is stripped from the adsorbent using this technique, the metallic reagent remaining in the adsorbent can be oxidized to its cationic form, which is effective for the application of the present invention. The procedure to oxidize the iodine-compound reactive metallic ingredient and to re-exchange the resulting cations with the active sites of the zeolite portion of the adsorbent is well known in the art. An oxygen-containing gas stream is often used for the oxidation procedure, and air is typically chosen for convenience. However, other oxidizing agents, such as oxygen, carbon monoxide, nitrogen oxide, and mixtures thereof are also acceptable even if they contain some impurities.

Within the scope of the present invention, it is possible to pass the treated liquid stream, which has been depleted in iodine-containing compounds to less than 10 and preferably less than 5 ppb (measured as total elemental iodine) by weight, over a second bed of the adsorbent, in which the zeolite component has not been cation-exchanged with an iodine-reactive metal. This serves to recover or "trap" any metallic cations originally present in the metal-exchanged zeolite-containing adsorbent that are released into the treated liquid stream due to displacement by hydrogen ions or any metallic cation contaminants in the pretreated liquid feed stream during the adsorption step. This procedure would therefore ensure that cations released from the adsorbent during the adsorption step of the present invention are retained within the system and therefore do not contaminate the treated liquid stream.

It is, of course, also within the scope of the present invention to periodically reverse the flow through the aforementioned two bed system to drive an active mass-transfer zone of metallic iodine-reactive cations from one bed to the other, thereby making them continually available for adsorption of the iodine-containing compounds in the pretreated liquid feed stream. Details associated with the operation of such a two bed system are well known to those skilled in the art. To scavenge any cations, including those used for adsorption of iodine-containing compounds, exiting with the treated liquid stream of the present invention, it is also possible to use any suitable commercial product selective for the adsorption of cations. Especially preferred for this service are cation exchange resins cited previously for use as a pretreatment medium in scavenging metal cation contaminants in the liquid feed stream. Included among these resins is, for example, Amberlyst® 15 in the hydrogen form.

The adsorption step can be performed using a fixed-, moving-, or fluidized-bed system or a batch operation. It is preferred to employ a fixed-bed system with the iodine-contaminated pretreated liquid feed stream continually flowing through the adsorption zone of active adsorbent. Of course, the adsorption step may also comprise a plurality of adsorption zones with the desired conditions maintained between and within the separate beds. In any case, depending on iodine-compound concentration in the pretreated liquid feed stream, the operating conditions of the adsorption step can be manipulated to achieve a treated liquid stream containing less than about 10 ppb by weight of total iodine and preferably less than about 5 ppb by weight. Regarding the mechanics of the operation of the adsorption step of the present invention, it is possible to use swing-bed systems of the prior art to alternate beds of adsorbent between the adsorption, reactivation, and regeneration steps.

What is claimed is:

1. A process for treating a liquid feed stream containing a contaminant comprising an iodine compound, the process comprising:
    a) pretreating the liquid feed stream to remove at least a portion of the contaminant and yield a pretreated liquid feed stream containing at least a residual amount of the iodine compound; and
    b) contacting the pretreated liquid feed stream with an adsorbent comprising a zeolite having a silica to alumina molar ratio from about 5 to less than 15 which has been cation exchanged with a metal selected from the group consisting of silver, mercury, copper, lead, thallium, palladium, and mixtures thereof, at adsorption conditions to adsorb at least a portion of the residual amount of iodine compound to yield a treated liquid stream.

2. The process of claim 1 where the liquid feed stream comprises an acetic acid feed stream.

3. The process of claim 1 where the zeolite has a silica to alumina molar ratio from about 8 to about 12.

4. The process of claim 1 where the zeolite is mordenite.

5. The process of claim 1 where the adsorbent further comprises an inorganic refractory metal oxide binder.

6. The process of claim 5 where the binder is selected from the group consisting of silica, titania, zirconia, chromia, boria, vanadia, magnesia, and mixtures thereof.

7. The process of claim 5 where the zeolite is selected from the group consisting of LZ-210, mordenite, steam stabilized Y zeolite, Y-85, and mixtures thereof.

8. The process of claim 7 where the zeolite is LZ-210.

9. The process of claim 1 where the metal is silver and is present, on an elemental basis, in an amount from about 1 to about 15 weight percent of the adsorbent.

10. The process of claim 1 where the iodine compound is an alkyl iodide having from 1 to 8 carbon atoms.

11. The process of claim 1 where the contaminant further comprises a metal selected from the group consisting of $Rh^{+3}$, $Ir^{+3}$, $Ru^{+3}$, $Os^{+3}$, $Re^{+5}$, $Co^{+2}$, $Ni^{+2}$, $Mo^{+5}$, $V^{+3}$, $Fe^{+3}$, $Ti^{+4}$, $Zr^{+4}$, and mixtures thereof.

12. The process of claim 1 where the adsorption conditions include a temperature from about 30° C. to about 150° C., pressure from about 1 to about 5 atmospheres, and a liquid hourly space velocity from about 0.1 to about 10 $hr^{-1}$.

13. The process of claim 1 where the treated liquid stream contains less than about 10 parts per billion of total iodine by weight.

14. The process of claim 1 where the pretreating comprises contacting the liquid feed stream with a pretreatment medium.

15. The process of claim 14 where the pretreatment medium is selected from the group consisting of zeolites, resins, and activated carbon.

16. The process of claim 1 where the pretreating comprises:
    a) contacting the liquid feed stream with ozone to yield an ozonated liquid stream and
    b) contacting the ozonated liquid stream with a pretreatment medium to provide the pretreated liquid feed stream.

17. The process of claim 16 where the pretreatment medium is selected from the group consisting of zeolites, resins, and activated carbon.

18. The process of claim 1 where the pretreating comprises:
    a) contacting the liquid feed stream with methanol to convert at least a portion of the iodine compound to methyl iodide and yield a methyl iodide-containing liquid stream and
    b) fractionating the methyl iodide-containing liquid stream to separate at least a portion of the methyl iodide therefrom in an overhead liquid stream and provide the pretreated liquid feed stream.

19. The process of claim 1 where the pretreating comprises:
    a) contacting the liquid feed stream with methanol to convert at least a portion of the iodine compound to methyl iodide and thereby yielding a methyl iodide-containing liquid stream,
    b) fractionating the methyl iodide-containing liquid stream to separate at least a portion of the methyl iodide therefrom in an overhead liquid stream and yield a bottoms liquid product stream, and
    c) contacting the bottoms liquid product stream with a pretreatment medium to provide the pretreated liquid stream.

20. The process of claim 19 where the pretreatment medium is selected from the group consisting of zeolites, resins, and activated carbon.

21. The process of claim 1 where the pretreating comprises:
    a) contacting the liquid feed stream with a salt or a hydroxide compound of a cation to convert at least a portion of the iodine compound to an iodide salt and thereby yielding an iodide salt-containing liquid stream, and
    b) fractionating the iodide salt-containing liquid stream to separate at least a portion of the iodide salt therefrom in a heavy ends liquid stream and provide the pretreated liquid feed stream.

22. The process of claim 21 where the cation is selected from the group consisting of $Na^+$, $K^+$, $Li^+$, $Mg^{+2}$, $Ca^{+2}$, and $NH_4^+$.

23. The process of claim 1 where the pretreating comprises:
    a) contacting the liquid feed stream with a salt or a hydroxide compound of a cation to convert at least a portion of the iodine compound to an iodide salt and thereby yielding an iodide salt-containing liquid stream b) fractionating the iodide salt-containing liquid feed stream to separate at least a portion of the iodide salt therefrom in a heavy ends liquid stream and yield a light ends liquid product stream, and c) contacting the light ends liquid product stream with a pretreatment medium to provide the pretreated liquid stream.

24. The process of claim 23 where the pretreatment medium is selected from the group consisting of zeolites, resins, and activated carbon.

25. The process of claim 23 where the cation is selected from the group consisting of $Na^+$, $K^+$, $Li^+$, $Mg^{+2}$, $Ca^{+2}$, and $NH_4^+$.

26. The process of claim 1 where the pretreating comprises:

a) contacting the liquid feed stream with methanol to convert at least a portion of the iodine compound to methyl iodide and yield a methyl iodide-containing liquid stream, b) fractionating the methyl iodide-containing liquid stream to separate at least a portion of the methyl iodide therefrom in an overhead liquid stream and yield a bottoms liquid product stream containing at least a portion of the iodine compound, c) contacting the bottoms liquid product stream with a salt or a hydroxide compound of a cation to convert at least a portion of the iodine compound therein to an iodide salt and thereby yielding an iodide salt-containing liquid stream, and d) fractionating the iodide salt-containing liquid stream to separate at least a portion of the iodide salt therefrom in a heavy ends liquid stream and provide the pretreated liquid feed stream.

27. The process of claim 26 where the cation is selected from the group consisting of $Na^+$, $K^+$, $Li^+$, $Mg^{+2}$, $Ca^{+2}$, and $NH_4^+$.

28. The process of claim 1 where the pretreating comprises:

a) contacting the liquid feed stream with methanol to convert at least a portion of the iodine compound to methyl iodide and yield a methyl iodide-containing liquid stream, b) fractionating the methyl iodide-containing liquid stream to separate at least a portion of the methyl iodide therefrom in an overhead liquid stream and yield a bottoms liquid product stream containing at least a portion of the iodine compound, c) contacting the bottoms liquid product stream with a salt or a hydroxide compound of a cation to convert at least a portion of the iodine compound therein to an iodide salt and thereby yielding an iodide salt-containing liquid stream, d) fractionating the iodide salt-containing liquid stream to separate at least a portion of the iodide salt therefrom in a heavy ends liquid stream and yield a light ends liquid product stream, and e) contacting the light ends liquid product stream with a pretreatment medium to provide the pretreated liquid stream.

29. The process of claim 28 where the pretreatment medium is selected from the group consisting of zeolites, resins, and activated carbon.

30. The process of claim 28 where the cation is selected from the group consisting of $Na^+$, $K^+$, $Li^+$, $Mg^{+2}$, $Ca^{+2}$, and $NH_4^+$.

31. The process of claim 1 further comprising, after step (b), fractionating the treated liquid stream to separate a heavy liquid fraction therefrom and yield an overhead liquid fraction substantially free of dissolved solids.

32. The process of claim 1 where the process is carried out until the adsorbent has substantially reached its adsorption capacity, at which point the adsorbent is reactivated by contacting it with a solution of a salt of a reactivation metal where the metal is selected from the group consisting of silver, mercury, copper, lead, thallium, palladium, and mixtures thereof such that an amount of reactivation metal is added to the adsorbent.

33. The process of claim 1 where the process is carried out until the adsorbent has substantially reached its adsorption capacity, at which point the adsorbent is contacted with a regenerant gas stream comprising hydrogen at conditions effective to strip substantially all of the adsorbed iodine as hydrogen iodide to yield a regenerated adsorbent.

34. The process of claim 33 where the regenerant gas stream comprises hydrogen and a diluent gas selected from the group consisting of nitrogen, argon, methane, ethane, propane, and mixtures thereof.

35. The process of claim 33 where the regenerated adsorbent is treated with an oxidizing gas such that the metal is oxidized.

36. The process of claim 35 where the oxidizing gas is selected from the group consisting of oxygen, air, carbon monoxide, nitrogen oxide, and mixtures thereof.

* * * * *